US011986487B2

(12) United States Patent
Vigsnæs et al.

(10) Patent No.: US 11,986,487 B2
(45) Date of Patent: *May 21, 2024

(54) MIXTURE OF HMOS FOR TREATING WHEAT SENSITIVITY

(71) Applicant: GLYCOM A/S, Hørsholm (DK)

(72) Inventors: Louise Kristine Vigsnæs, Copenhagen NV (DK); Bruce McConnell, La Tour de Peilz (CH)

(73) Assignee: GLYCOM A/S, Hørsholm (DK)

(*) Notice: Subject to any disclaimer, the term of this patent is extended or adjusted under 35 U.S.C. 154(b) by 0 days.

This patent is subject to a terminal disclaimer.

(21) Appl. No.: 17/934,123

(22) Filed: Sep. 21, 2022

(65) Prior Publication Data

US 2023/0014752 A1      Jan. 19, 2023

Related U.S. Application Data

(63) Continuation of application No. 16/768,333, filed as application No. PCT/IB2018/059497 on Nov. 30, 2018, now Pat. No. 11,452,736.

(30) Foreign Application Priority Data

Nov. 30, 2017   (DK) .......................... PA 2017 00680

(51) Int. Cl.
| | | |
|---|---|---|
| *A61K 31/702* | (2006.01) | |
| *A23L 33/00* | (2016.01) | |
| *A23L 33/21* | (2016.01) | |
| *A61P 1/00* | (2006.01) | |

(52) U.S. Cl.
CPC ............ *A61K 31/702* (2013.01); *A23L 33/21* (2016.08); *A23L 33/40* (2016.08); *A61P 1/00* (2018.01)

(58) Field of Classification Search
None
See application file for complete search history.

(56) References Cited

U.S. PATENT DOCUMENTS

| | | |
|---|---|---|
| 2012/0172319 A1 | 7/2012 | Chow et al. |
| 2014/0187474 A1 | 7/2014 | Sonnenburg |
| 2015/0320778 A1 | 11/2015 | Chow et al. |
| 2015/0329580 A1 | 11/2015 | Podányi et al. |
| 2016/0296543 A1 | 10/2016 | Brassart et al. |
| 2016/0310514 A1 | 10/2016 | Salomonsson et al. |
| 2017/0000830 A1 | 1/2017 | Saini |

FOREIGN PATENT DOCUMENTS

| | | |
|---|---|---|
| CN | 103402376 | 11/2013 |
| CN | 103763940 | 4/2014 |
| CN | 104822279 | 8/2015 |
| CN | 105682664 | 6/2016 |
| CN | 106794207 | 5/2017 |
| CN | 107106584 | 8/2017 |
| WO | 0104341 A1 | 1/2001 |
| WO | 2007101862 A1 | 9/2007 |
| WO | 2010115934 A1 | 10/2010 |
| WO | 2010115935 A1 | 10/2010 |
| WO | 2011005681 A1 | 1/2011 |
| WO | 2011100979 A1 | 8/2011 |
| WO | 2011100980 A1 | 8/2011 |
| WO | 2012007588 A9 | 7/2012 |
| WO | WO 2012092155 | 7/2012 |
| WO | WO 2012092160 | 7/2012 |
| WO | 2012113404 A1 | 8/2012 |
| WO | 2012113405 A1 | 8/2012 |
| WO | 2012127410 A1 | 9/2012 |
| WO | 2012155916 A1 | 11/2012 |
| WO | 2012156897 A1 | 11/2012 |
| WO | 2012156898 A1 | 11/2012 |
| WO | 2013025104 A1 | 2/2013 |
| WO | 2013044928 A1 | 4/2013 |
| WO | 2013091660 A1 | 6/2013 |
| WO | 2013139344 A1 | 9/2013 |
| WO | WO 2014201037 | 12/2014 |
| WO | 2016066175 A1 | 5/2016 |
| WO | WO 2016066763 | 5/2016 |
| WO | 2017046711 A1 | 3/2017 |
| WO | 2017190754 A1 | 11/2017 |
| WO | 2018187792 A1 | 10/2018 |
| WO | 2019111115 A2 | 6/2019 |
| WO | 2019123316 A1 | 6/2019 |

OTHER PUBLICATIONS

U.S. Appl. No. 16/768,333, filed May 29, 2020.
Bode, L., "(2013) Human milk oligosaccharides and their beneficial effects", Handbook of dietary and nutritional aspects of human breast milk Human Health Handbooks No. 5. (pp. 515-531) the Netherlands: Wageningen Academic Publishers.
Bottacini, F., et al., "Diversity, ecology and intestinal function of bifidobacteria", Microbial Cell Factories, 2014, vol. 13, pp. 1-15.
Catassi, C., et al., "The Overlapping Area of Non-Celiac Gluten Sensitivity (NCGS) and Wheat-Sensitive Irritable Bowel Syndrome (IBS): An Update", Nutrients, 2017, vol. 9, 16 pages, doi:10.3390/nu9111268.
Chen, Xi, "Human Milk Oligosaccharides (HMOS): Structure, Function, and Enzyme-Catalyzed Synthesis", Advances in Carbohydrate Chemistry and Biochemistry, 2015, vol. 72, pp. 113-190.
Duranti, S., et al., "Exploration of the Genomic Diversity and Core Genome of the Bifidobacterium adolescentis Phylogenetic Group by Means of a Polyphasic Approach", Applied and Environmental Microbiology, 2013, vol. 79(1), pp. 336-346.

(Continued)

*Primary Examiner* — Dale R Miller

(74) *Attorney, Agent, or Firm* — Neal, Gerber & Eisenberg LLP

(57) ABSTRACT

The invention relates to a human milk oligosaccharide (HMO) for use in, a synthetic composition comprising an HMO for use in, and a method for the treatment of, secondary prevention of, and/or induction of tolerance to non-coeliac wheat and/or gluten sensitivity in a human.

19 Claims, No Drawings

(56) References Cited

OTHER PUBLICATIONS

European Commission, "(2017) Commission Notice on the classification of Food for Special Medical Purposes," Official Journal of the European Union, C 401, pp. 1-15.
Leccioli, V., et al., "A New Proposal for the Pathogenic Mechanism of Non-Coeliac/Non-Allergic Gluten/Wheat Sensitivity: Piecing Together the Puzzle of Recent Scientific Evidence", Nutrients, 2017, vol. 9, 25 pages. doi: 10.3390/nu9111203.
Uhde, M., et al., "Intestinal cell damage and systemic immune activation in individuals reporting sensitivity to wheat in the absence of coeliac disease", Gut, 2016, vol. 65, pp. 1930-1937.
Urashima, T., et al., (2011) Nutrition and Diet Research Progress: Milk Oligosaccharides. New York: Nova Science Publishers, Inc. 92 pages.
Adams, C.A., et al., "The benefits of human milk oligosaccharides in adult nutrition," Nutrafoods, 2018, vol. 17, pp. 169-173. Retrieved from http://jennewein-biotech.de/cms/assets/uploads/2018/11/ArticleNutrafoodsNov2018.pdf.
Leonard, M.M. et al., "Celiac Disease and Nonceliac Gluten Sensitivity: A Review," The Journal of the American Medical Association, 2017, vol. 318(7), pp. 647-656.
Sollid, L.M., "Breast milk against coeliac disease," Gut, 2002, vol. 51(6), pp. 767-768.
Catassi, C., et al., "Diagnosis of Non-Celiac Gluten Sensitivity (NCGS): The Salerno Experts' Criteria," Nutrients, 2015, vol. 7, pp. 4966-4977.
Cozma, A.I., et al., "The Role of Fructose, Sucrose and High-fructose Corn Syrup in Diabetes," European Endocrinology, 2014, vol. 10, pp. 51-60.
Mocan, O., et al., "The Broad Spectrum of Celiac Disease and Gluten Sensitive Enteropathy," Clujul Medical, 2016, vol. 89(3), pp. 335-342.
Ng, Q.X., et al., "The role of inflammation in irritable bowel syndrome (IBS)," Journal of Inflammation Research, 2018, vol. 11, pp. 345-349.
Puccetti, A., et al., "Immune Response to Rotavirus and Gluten Sensitivity," Journal of Immunology Research, 2018, vol. 2018, 26 pages, https://doi.org/10.1155/2018/9419204.
Rinninella, E., et al., "Food Components and Dietary Habits: Keys for a Healthy Gut Microbiota Composition," Nutrients, 2019, vol. 11, 23 pages, doi:10.3390/nu11102393.
Mitselou, A., et al., "Proinflammatory cytokines in irritable bowel syndrome: a comparison with inflammatory bowel disease," Intest Res, 2020, vol. 18(1), pp. 115-120.
Bode, L. (2012). Human milk oligosaccharides: every baby needs a sugar mama. Glycobiology, 22(9), 1147-1162. (Year: 2012).
Elison, et al., "Oral supplmentation of healthy adults with 2'-O-fucosyllactose and lacto-N-neotetraose is well tolerated and shifts the intenstinal microbiota," Br J Nutr. (2016), 116(8): 1356-1368, 12 pp.
Tarr, et al., "The prebiotics 3'Sialyllactose and 6'Sialyllactose diminsh stressor-induced anxiety-like behavior and colonic microbiota alterations: Evidence for effects on the gut-brain axis," Brain Behav Immun. (2015), 50: 166-177, 11 pp.

MIXTURE OF HMOS FOR TREATING WHEAT SENSITIVITY

CROSS-REFERENCE TO RELATED APPLICATIONS

This application is a continuation application of U.S. application Ser. No. 16/768,333, filed on May 29, 2020, which is a national stage entry pursuant to 35 U.S.C. § 371 of International Patent Application No. PCT/IB2018/059497, filed on Nov. 30, 2018, which claims priority to Denmark Application No. PA 2017 00680, filed on Nov. 30, 2017, the contents of all of which are fully incorporated herein by reference.

FIELD OF THE INVENTION

This invention relates to a method, compounds and composition for the prevention and/or treatment of non-coeliac wheat sensitivity.

BACKGROUND OF THE INVENTION

Non-coeliac wheat sensitivity, which is also known as non-coeliac gluten sensitivity, is a gluten-related disorder along with coeliac disease and wheat allergy (Leccioli et al. *Nutrients* 9, 1203 (2017)). Non-coeliac wheat sensitivity is a non-allergic and non-autoimmune condition in which the consumption of wheat and/or gluten can lead to symptoms similar to those seen in other gluten-related disorders. The condition is viewed as a wheat and/or gluten sensitivity because symptoms are relieved by wheat and/or gluten withdrawal and re-appear upon reintroduction of wheat and/or gluten. However, patients having the condition do not exhibit the characteristic autoimmune or allergy markers associated with coeliac disease or gluten allergy. Despite this, the clinical symptoms are similar to those of coeliac disease and gluten allergy.

The most frequent gastrointestinal symptoms include bloating, abdominal pain, epigastric pain, diarrhoea, and constipation. Non-gastrointestinal symptoms include tiredness, headache, anxiety, "foggy mind" or difficulty focusing, depression and skin rash. These symptoms can occur within hours to days following exposure to wheat and/or gluten and can then dissipate upon withdrawal of the wheat and/or gluten.

The aetiology of non-coeliac wheat sensitivity is unknown. The condition potentially involves many triggers as are seen in coeliac disease and gluten allergy. The initiating trigger mainly involves exposure of gut epithelium to wheat and/or gluten leading to immune-mediated and/or non-immune mediated responses. Due to the lack of evidence for T-cell involvement and the apparent involvement of toll-like receptors (TLR), the condition may be more of an innate immune response rather than adaptive immune response.

Since specific triggers have not been identified, the condition could involve different mechanisms from coeliac disease and gluten allergy. Gluten, the trigger in coeliac disease, may be a significant trigger in the condition but there are increasing doubts whether it is the main trigger or a trigger at all. Several other food-derived stimuli may also be important triggers. These include alpha amylase/trypsin inhibitors (ATIs), fermentable oligo-, di-, monosaccharides and polyols (FODMAPS) and other short chain fructans. ATIs, in particular, have been implicated in the pathology. The role of ATIs in mounting an immunological response has been shown in animal and human research models and is believed to be an important oral antigen both in coeliac disease and in non-coeliac wheat sensitivity. ATIs trigger predominantly innate immune responses involving macrophages, neutrophils and intestinal dendritic cells via activation of the TLR complexes. Contrary, gliadin does not appear to be a major trigger because typical gliadin-induced enteric responses are not characteristically seen, and in addition, gliadin primarily activates adaptive immunity markers (e.g. IL-6, IL-21 and INF-γ), which has not been found in patients having non-coeliac wheat sensitivity.

Patients having non-coeliac wheat sensitivity show increased levels of TLR2 expression, increased number of α and β intraepithelial lymphocytes, and reduced number of T-regulatory cells. Also, these patients have increased levels of lipopolysaccharide binding protein (LBP) and soluble CD14 proteins. In addition, these patients have elevated circulating levels of fatty acid-binding protein 2 (FABP2), a marker of intestinal epithelial cell damage (Uhde et al. *Gut* 65, 1930 (2016)). It is now accepted that patients having non-coeliac wheat sensitivity show increased intestinal permeability which allows antigens to cross into the lamina propria.

Changes in the gut microbiota may also play a role in non-coeliac wheat sensitivity. The immune markers seen in the patients are predominantly innate immune response markers and this provides evidence of the microbiota having a role. However, the evidence for the role of the microbiota is not yet clear. From a compositional perspective, it appears that patients may have lower abundance of butyrate-producing bacteria and bifidobacteria.

Additionally, there is some evidence for the condition developing in individuals with some genetic predispositions. The genetic predisposition is higher than general population but lower than patients with coeliac disease, who have a strong genetic component. However, this association with genes is currently not clear.

Diagnosis of the condition is complex and many patients are unwilling to go through the process. The 1st step in a diagnosis is the exclusion of coeliac disease and wheat and/or gluten allergy. This is done by placing the patient on a gluten containing diet for a 6-week period. Several tests are performed during this period to exclude wheat allergy, namely wheat specific IgE and skin prick test, and coeliac disease, namely IgA-tTG, IgG-DGP and IgA-EMA. If necessary, a duodenal biopsy can be taken for confirmation. The 2nd step consists of starting the patient on a gluten-free diet for a 6-week period and monitoring for symptom response. This symptom response is evaluated using the gastrointestinal symptom rating scale (GSRS) and a numerical rating scale (NRS). If the patient fails to show an improvement in symptoms in 6 weeks upon commencement of the diet, diagnosis of the condition is ruled out and other diagnoses such as IBS and other functional bowel disorders need to be explored. The 3rd step involves the re-introduction of the gluten containing diet. In this step, the patient is randomly assigned into one of two protocols. The patient is exposed to either gluten-free diet+placebo or a gluten-free diet+gluten for a week. The patient is then put on a 1-week washout period of a strict gluten-free diet, followed by a crossover for 1 week. A 30% symptomatic improvement on introduction of the diet free from gluten or a 30% symptomatic appearance on introduction of the gluten containing diet indicates a positive result. Below this 30% value, a negative result is considered.

The difficulty in diagnosis means that the prevalence of the condition is not clear. However, the condition is becoming a more common diagnosis. As a result, the prevalence of the condition has been reported to vary enormously from 0.6-6% in Western populations. This lack of ability to diagnose results in patients starting a gluten-free diet after self-diagnosis without any formal clinical testing or management recommendation by their physician. Due to this, the consumption of gluten free food has become increasingly popular in the Western world. A Gallup poll conducted in July 2015 showed that 20% of Americans opt for a gluten free diet while 17% say they avoid gluten free foods.

Currently, there is no cure for the condition and the only accepted treatment is to place the patient on a gluten-free diet and this often helps resolve the intestinal and extra intestinal symptoms. However, the recommendation is then to continue with the gluten-free diet for life. The nutritional consequences of this are unclear because grains which contain gluten also contain many essential nutrients; especially fibres. Also, removing gluten-containing foods can have a significant impact on the patient's quality of life. It would be better to be able to provide the patient with an intervention which at least sufficiently reduces symptoms or prevents reoccurrence of the condition even if wheat and/or gluten is consumed.

Therefore, there remains a need for methods and compounds for the management of non-coeliac wheat and/or gluten sensitivity in humans which would allow consumption of wheat and/or gluten.

SUMMARY OF THE INVENTION

A first aspect of the invention relates to a human milk oligosaccharide (HMO) for use in:
  the treatment of non-coeliac wheat and/or gluten sensitivity in a human,
  inducing wheat and/or gluten tolerance in a patient suffering from non-coeliac wheat and/or gluten sensitivity, and/or
  the secondary prevention of non-coeliac wheat and/or gluten sensitivity in a human.

A second aspect of the invention relates to a synthetic composition for use in:
  the treatment of non-coeliac wheat and/or gluten sensitivity in a human,
  inducing wheat and/or gluten tolerance in a patient suffering from non-coeliac wheat and/or gluten sensitivity, and/or
  the secondary prevention of non-coeliac wheat and/or gluten sensitivity in a human, the composition comprising at least one human milk oligosaccharide (HMO).

Preferably the synthetic composition contains an amount of 1 g to 15 g of the HMO; more preferably 2 g to 10 g. For example, the synthetic composition may contain 3 g to 7 g of the HMO.

The synthetic composition may contain a bifidobacteria, for example *Bifidobacterium longum* and/or *Bifidobacterium bifidum*.

A third aspect of the invention relates to a method for treatment of non-coeliac wheat and/or gluten sensitivity in a human, the method comprising administering to the human an effective amount of at least one human milk oligosaccharide (HMO).

A fourth aspect of the invention relates to a method for the secondary prevention of non-coeliac wheat and/or gluten sensitivity in a human, the method comprising administering to the human an effective amount of at least one human milk oligosaccharide (HMO).

A fifth aspect of the invention relates to a method for inducing wheat and/or gluten tolerance in a patient suffering from non-coeliac wheat and/or gluten sensitivity, the method comprising administering to the patient an effective amount of at least one human milk oligosaccharide (HMO).

Preferably, the patient is administered the HMO while consuming gluten containing cereals.

The amount of the HMO administered is preferably effective to increase the abundance of butyrate-producing bacteria and/or bifidobacteria in the intestine of the human. Further, the amount of the HMO administered is preferably effective to improve the intestinal barrier properties of the human, particularly in the colon.

Preferably, the human is administered an amount of 1 g to 15 g per day of the HMO, more preferably 2 g to 10 g per day. For example, the human may be administered 3 g to 7 g per day. Preferably, the human is administered the HMO for a period of at least 7 consecutive days (1 week), more preferably for at least 14 consecutive days (2 weeks).

The patient may be administered higher doses during treatment of non-coeliac wheat and/or gluten sensitivity and lower doses to induce wheat and/or gluten tolerance or as secondary prevention. Preferably the human is administered the HMO for a period of at least 1 week, more preferably for at least 2 weeks during treatment. The human may be administered the HMO for a period of at least 4 weeks, more preferably for at least 8 weeks to induce wheat and/or gluten tolerance or as secondary prevention. The dose administered during a treatment phase is preferably about 3 g to about 15 g per day (for example about 4 g to about 7.5 g per day) and the dose administered during the wheat and/or gluten tolerance inducing or the secondary prevention phase is preferably about 2 g to about 7.5 g per day (for example about 2 g to about 5 g per day). In one embodiment, the method of invention comprises a first phase to treat the non-coeliac wheat and/or gluten sensitivity which is followed by a second phase for inducing the wheat and/or gluten tolerance or the secondary prevention. Preferably, in the first phase, the human is administered the HMO for a period of at least 7 consecutive days (1 week), more preferably for at least 14 consecutive days (2 weeks) until the non-coeliac wheat and/or gluten sensitivity ameliorates (typically 2-3 months) followed by the second phase to induce wheat and/or gluten tolerance or as secondary prevention in which human is administered the HMO for a period of at least 4 (consecutive) weeks, more preferably for at least 8 weeks.

A sixth aspect of this invention relates to a pack for use in:
  the treatment of non-coeliac wheat and/or gluten sensitivity in a human,
  inducing wheat and/or gluten tolerance in a patient suffering from non-coeliac wheat and/or gluten sensitivity, and/or
  the secondary prevention of non-coeliac wheat and/or gluten sensitivity in a human, the pack comprising at least 14 individual daily doses of an effective amount of at least one human milk oligosaccharide (HMO).

Preferably, each dose contains about 1 g to about 15 g of the human milk oligosaccharide, more preferably about 2 g to about 10 g; for example, about 3 g to about 7 g. Preferably, the pack comprises at least 21 individual daily doses; more preferably at least 28 daily doses; for example, at least 35 daily doses. The pack can include instructions for use.

A seventh aspect of the invention is a use of
  one or more human milk oligosaccharides (HMOs),
  a synthetic composition comprising one or more human milk oligosaccharides (HMOs), or a pack comprising at least 14 individual daily doses of an effective amount of one or more human milk oligosaccharides in the dietary management of a patient suffering from non-coeliac wheat and/or gluten sensitivity.

In certain embodiments of any of the aspects above, the HMO can be a neutral HMO or an acidic HMO. The neutral HMO can be one or more fucosylated HMOs or one or more non-fucosylated HMOs. Preferably the HMO is selected from 2'-FL, 3-FL, DFL, LNT, LNnT, 3'-SL, 6'-SL, LNFP-I or a mixture thereof. Preferably the HMO comprises, consists of or essentially consists of 2'-FL and at least one of LNnT and LNT; at least one of 2'-FL and DFL and at least one of LNnT and LNT (e.g. 2'-FL, DFL and at least one of LNnT and LNT); 2'-FL and 6'-SL; DFL and 6'-SL; 2'-FL, DFL and 6'-SL; 2'-FL, 6'-SL and at least one of LNnT and LNT; and 2'-FL, DFL, 6'-SL and at least one of LNnT and/or LNT.

DETAILED DESCRIPTION OF THE INVENTION

It has now been surprisingly found that oral or enteral administration of one or more human milk oligosaccharides (HMOs) to patients suffering from non-coeliac wheat and/or gluten sensitivity reduces symptoms of the condition. Furthermore, the HMOs surprisingly induce tolerance to wheat and/or gluten patients suffering from non-coeliac wheat and/or gluten sensitivity; allowing patients to consume wheat and/or gluten with reduced or no symptoms. Therefore, human milk oligosaccharides may be used as a dietary secondary prevention of non-coeliac wheat and/or gluten sensitivity. The HMOs also preferentially increase the abundance of bifidobacteria in the gastro-intestinal tract, in particular bifidobacteria of the *B. adolescentis* phylogenetic group, *Bifidobacterium longum* and/or *Bifidobacterium bifidum*. These bacteria produce lactate and acetate which in turn can be converted into butyrate by butyrate-producing bacteria.

Human milk oligosaccharides are a heterogeneous mixture of soluble glycans found in human milk. They are the third most abundant solid component after lactose and lipids in human milk and are present in concentrations of 5-25 g/l (Bode: Human milk oligosaccharides and their beneficial effects, in: Handbook of dietary and nutritional aspects of human breast milk (Zibadi et al., eds.), pp. 515-31, Wageningen Academic Publishers (2013)). HMOs are resistant to enzymatic hydrolysis in the small intestine and are thus largely undigested and unabsorbed and reach the colon intact. Most of the HMOs that reach the colon serve as substrates to shape the gut ecosystem by selectively stimulating the growth of specific bacteria. HMOs are believed to substantially modulate the infant gut microbiota and play a decisive role in the differences in the microbiota of formula-fed and breast-fed infants. These differences include the predominance of *Bifidobacterium* in the gut of breast-fed infants compared to a more diverse gut microbiota in formula-fed infants. This is viewed as beneficial for the infant because strains of *Bifidobacterium* species are believed to have a positive effect on gut health.

The HMOs also preferentially increase the abundance of bifidobacteria in the gastro-intestinal tract, in particular bifidobacteria of the *B. adolescentis* phylogenetic group, *Bifidobacterium longum* and/or *Bifidobacterium bifidum*.

In this specification, the following terms have the following meanings:

"Non-coeliac wheat sensitivity" means is a syndrome characterised by intestinal and extra-intestinal symptoms related to the ingestion of gluten-containing food, in subjects that are not affected by either coeliac disease or wheat allergy. "Non-coeliac gluten sensitivity" has the same meaning and the two terms are used interchangeably. The gluten-containing food usually contains a gluten-containing cereal such as wheat, barley and rye.

"Non-infant human" or "non-infant" means a human of 3 years of age and older. A non-infant human can be a child, a teenager, an adult or an elderly person.

"Human milk oligosaccharide" or "HMO" means a complex carbohydrate found in human breast milk (Urashima et al.: Milk Oligosaccharides. Nova Science Publisher (2011); Chen *Adv. Carbohydr. Chem. Biochem.* 72, 113 (2015)). The HMOs have a core structure comprising a lactose unit at the reducing end that can be elongated by one or more β-N-acetyl-lactosaminyl and/or one or β-more lacto-N-biosyl units, and which core structure can be substituted by an α L-fucopyranosyl and/or an α-N-acetyl-neuraminyl (sialyl) moiety. In this regard, the non-acidic (or neutral) HMOs are devoid of a sialyl residue, and the acidic HMOs have at least one sialyl residue in their structure. The non-acidic (or neutral) HMOs can be fucosylated or non-fucosylated. Examples of such neutral non-fucosylated HMOs include lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH). Examples of neutral fucosylated HMOs include 2'-fucosyllactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-fucopentaose VI (LNFP-VI), lacto-N-difucohexaose II (LNDFH-II), fucosyl-lacto-N-hexaose 1 (FLNH-I), fucosyl-para-lacto-N-hexaose I (FpLNH-I), fucosyl-para-lacto-N-neohexaose II (FpLNnH II) and fucosyl-lacto-N-neohexaose (FLNnH). Examples of acidic HMOs include 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), LST c, fucosyl-LST c (FLST c), sialyl-LNH (SLNH), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DSLNT).

"Synthetic composition" means a composition which is artificially prepared and preferably means a composition containing at least one compound that is produced ex vivo chemically and/or biologically, e.g. by means of chemical reaction, enzymatic reaction or recombinantly. In some embodiments, a synthetic composition of the invention may be, but preferably is not, identical with a naturally occurring composition. The synthetic composition typically comprises one or more compounds, including one or more HMOs, that are capable of reducing symptoms of wheat and/or gluten sensitivity in a human or inducing tolerance. Also, in some embodiments, the synthetic compositions may comprise one or more nutritionally or pharmaceutically active components which do not affect adversely the efficacy of the above-mentioned compounds. Some non-limiting embodiments of a synthetic composition of the invention are also described below.

"Microbiota", "microflora" and "microbiome" mean a community of living microorganisms that typically inhabits a bodily organ or part, particularly the gastro-intestinal organs of humans. The most dominant members of the gastrointestinal microbiota include microorganisms of the phyla of *Firmicutes, Bacteroidetes, Actinobacteria, Proteobacteria, Synergistetes, Verrucomicrobia, Fusobacteria*, and *Euryarchaeota*; at genus level *Bacteroides, Faecalibacterium, Bifidobacterium, Roseburia, Alistipes, Collinsella, Blautia, Coprococcus, Ruminococcus, Eubacterium* and *Dorea*; at species level Bacteroides uniformis, Alistipes putredinis, Parabacteroides merdae, Ruminococcus bromii, Dorea longicatena, Bacteroides caccae, Bacteroides thetaiotaomicron, Eubacterium hallii, *Ruminococcus torques, Faecalibacterium prausnitzii, Ruminococcus lactaris, Collinsella aerofaciens, Dorea formicigenerans, Bacteroides vulgatus* and *Roseburia intestinalis*. The gastrointestinal microbiota includes the mucosa-associated microbiota, which is located in or attached to the mucous layer covering the epithelium of the gastrointestinal tract, and luminal-associated microbiota, which is found in the lumen of the gastrointestinal tract.

"Enteral administration" means any conventional form for delivery of a composition to a non-infant that causes the deposition of the composition in the gastrointestinal tract (including the stomach). Methods of enteral administration include feeding through a naso-gastric tube or jejunum tube, oral, sublingual and rectal. "Oral administration" means any conventional form for the delivery of a composition to a human through the mouth. Accordingly, oral administration is a form of enteral administration.

"Effective amount" means an amount of a composition that provides an HMO in a sufficient amount to render a desired treatment outcome in a human. An effective amount can be administered in one or more doses to achieve the desired treatment outcome.

"Relative abundance of a bifidobacteria" means the abundance of a bifidobacteria species relative to other bifidobacteria in the microbiota of the gastro-intestinal tract of humans.

"Relative growth of a bifidobacteria" means the growth of a *Bifidobacterium* species relative to other bifidobacteria in the microbiota in the gastro-intestinal tract of humans.

"*Bifidobacterium* of the *B. adolescentis* phylogenetic group" means a bacterium selected from a group consisting of *Bifidobacterium adolescentis, Bifidobacterium angulatum, Bifidobacterium catenulatum, Bifidobacterium pseudocatenulatum, Bifidobacterium kashiwanohense, Bifidobacterium dentum* and *Bifidobacterium stercoris* (Duranti et al. *AppL Environ. Microbiol.* 79, 336 (2013), Bottacini et al. *Microbial Cell Fact.* 13:S4 (2014)). Preferably, a *Bifidobacterium* of the *B. adolescentis* phylogenetic group is *Bifidobacterium adolescentis* and/or *Bifidobacterium pseudocatenulatum*.

"Treat" means to address a medical condition or disease with the objective of improving or stabilising an outcome in the person being treated or addressing an underlying nutritional need. Treat, therefore, includes the dietary or nutritional management of the medical condition or disease by addressing nutritional needs of the person being treated. "Treating" and "treatment" have grammatically corresponding meanings.

"Dietary management" means exclusive or partial feeding of patients who, because of a disease, disorder or medical condition are suffering from:
  either have a limited, impaired or disturbed capacity to take, digest, absorb, metabolise or excrete ordinary food or certain nutrients contained therein, or metabolites, or
  have other medically-determined nutrient requirements (see: Commission Notice on the classification of Food for Special Medical Purposes of the European Commission, *Official Journal of the European Union* C 401, 25.11.2017, p. 10-11).

"Modulating of microbiota" means exerting a modifying or controlling influence on microbiota, for example an influence leading to an increase in the indigenous intestinal abundance of *Bifidobacterium, Barnesiella, Faecalibacterium* and/or other butyrate producing bacteria. In another example, the influence may lead to a reduction of the intestinal abundance of *Ruminococcus* gnavus and/or Proteobacteria. "Proteobacteria" are a phylum of Gram-negative bacteria and include a wide variety of pathogenic bacteria, such as *Escherichia, Salmonella, Vibrio, Helicobacter, Yersinia* and many other notable genera.

"Therapy" means treatment given or action taken to reduce or eliminate symptoms of a disease or pathological condition.

"Preventive treatment" or "prevention" in the present context means treatment given or action taken to diminish the risk of onset or recurrence of a disease.

"Secondary prevention" means prevention of onset of the condition in a high-risk patient, or prevention of reoccurrence of symptoms in a patient who has already has the condition. A "high-risk" patient is an individual who is predisposed to developing the condition; for example a person with a family history of the condition.

The HMOs can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies. As examples, using chemistry LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2010/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides can be made as described in WO 2012/156897 and WO 2012/156898. Biotechnological methods which describe how to make core (non-fucosylated neutral) human milk oligosaccharides optionally substituted by fucose or sialic acid using genetically modified *E. coli* can be found in WO 01/04341 and WO 2007/101862.

The HMO, in any of the above aspects, may be a single HMO or a mixture of any HMOs suitable for the purpose of the invention. The HMO can be a neutral HMO or an acidic HMO. The neutral HMO is, in one embodiment, one or more fucosylated HMOs; in another embodiment, the neutral HMO is one or more non-fucosylated HMOs. Particularly, the fucosylated neutral HMO is selected from the list consisting of 2'-FL, 3-FL, DFL, LNFP-I, LNFP-II, LNFP-III, LNFP-V, LNFP-VI, LNDFH-I, LNDFH-II, LNDFH-III, FLNH-I, FLNH-II, FLNnH, FpLNH-I and F-pLNnH II, preferably, 2'-FL, and the non-fucosylated neutral HMO is selected from the list consisting of LNT, LNnT, LNH, LNnH, pLNH and pLNnH, e.g. LNnT. The one or more fucosylated HMOs can be e.g. a mixture containing, consisting or consisting essentially of 2'-FL and DFL.

In one embodiment, the mixture comprises, consists of or essentially consists of, neutral HMOs, preferably at least a first neutral HMO and at least a second neutral HMO, wherein the first neutral HMO is a fucosylated neutral HMO and the second neutral HMO is a non-fucosylated neutral HMO. The fucosylated neutral HMO(s) and the non-fucosylated neutral HMO(s) may be present in a mass ratio of about 4:1 to 1:1. Particularly, the mixture of HMOs comprises, consists of or essentially consists of a fucosylated HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-I I, FLNnH, FpLNH-I and F-pLNnH II, and a non-fucosylated neutral HMO selected from the list consisting of LNT, LNnT, LNH, LNnH, pLNH and pLNnH. More preferably, the mixture of neutral HMOs contains, consists of or essentially consists of, a fucosylated HMO selected from the list consisting of 2'-FL, 3-FL and DFL, and a non-fucosylated neutral HMO selected from the list consisting of LNT and LNnT; advantageously the mixture comprises, consists of or essentially consists of, 2'-FL and at least one of LNnT and LNT; or at least one of 2'-FL and DFL and at least one of LNnT and LNT; or 2'-FL, DFL and at least one of LNnT and LNT.

In other embodiment, the mixture comprises, consists of or essentially consists of, at least a first (acidic) HMO and at least a second (neutral) HMO, wherein the first (acidic) HMO is selected from the list consisting of 3'-SL, 6'-SL and FSL and the second (neutral) HMO is selected from the list consisting of 2'-FL, 3-FL, DFL, LNT and LNnT; advantageously the mixture comprises, consists of or essentially consists of, 2'-FL and 6'-SL; or 6'-SL and at least one of 2'-FL and DFL; or 2'-FL, 6'-SL and at least one of LNnT and LNT; or 2'-FL, DFL, 6'-SL and at least one of LNnT and/or LNT.

Furthermore, in one embodiment, the synthetic composition can be in the form of a nutritional composition. For example, the nutritional composition can be a food composition, a rehydration solution, a medical food or food for special medical purposes, a nutritional supplement and the like. The nutritional composition can contain sources of protein, lipids and/or digestible carbohydrates and can be in powdered or liquid forms. The composition can be designed to be the sole source of nutrition or as a nutritional supplement.

Suitable protein sources include milk proteins, soy protein, rice protein, pea protein and oat protein, or mixtures thereof. Milk proteins can be in the form of milk protein concentrates, milk protein isolates, whey protein or casein, or mixtures of both. The protein can be whole protein or hydrolysed protein, either partially hydrolysed or extensively hydrolysed. Hydrolysed protein offers the advantage of easier digestion which can be important for humans with inflamed or compromised GI tracts. The protein can also be provided in the form of free amino acids. The protein can comprise about 5% to about 30% of the energy of the nutritional composition, normally about 10% to 20%.

The protein source can be a source of glutamine, threonine, cysteine, serine, proline, or a combination of these amino acids. The glutamine source can be a glutamine dipeptide and/or a glutamine enriched protein. Glutamine can be included due to the use of glutamine by enterocytes as an energy source. Threonine, serine and proline are important amino acids for the production of mucin. Mucin coats the GI tract and can improve intestinal barrier function and mucosal healing. Cysteine is a major precursor of glutathione, which is key for the antioxidant defences of the body.

Suitable digestible carbohydrates include maltodextrin, hydrolysed or modified starch or corn starch, glucose polymers, corn syrup, corn syrup solids, high fructose corn syrup, rice-derived carbohydrates, pea-derived carbohydrates, potato-derived carbohydrates, tapioca, sucrose, glucose, fructose, sucrose, lactose, honey, sugar alcohols (e.g. maltitol, erythritol, sorbitol), or mixtures thereof. Preferably the composition is reduced in or free from added lactose or other FODMAP carbohydrates. Generally digestible carbohydrates provide about 35% to about 55% of the energy of the nutritional composition. A particularly suitable digestible carbohydrate is a low dextrose equivalent (DE) maltodextrin.

Suitable lipids include medium chain triglycerides (MCT) and long chain triglycerides (LCT). Preferably the lipid is a mixture of MCTs and LCTs. For example, MCTs can comprise about 30% to about 70% by weight of the lipids, more specifically about 50% to about 60% by weight. MCTs offer the advantage of easier digestion which can be important for humans with inflamed or compromised GI tracts. Generally, the lipids provide about 35% to about 50% of the energy of the nutritional composition. The lipids can contain essential fatty acids (omega-3 and omega-6 fatty acids). Preferably these polyunsaturated fatty acids provide less than about 30% of total energy of the lipid source.

Suitable sources of long chain triglycerides are rapeseed oil, sunflower seed oil, palm oil, soy oil, milk fat, corn oil, high oleic oils, and soy lecithin. Fractionated coconut oils are a suitable source of medium chain triglycerides. The lipid profile of the nutritional composition is preferably designed to have a polyunsaturated fatty acid omega-6 (n−6) to omega-3 (n−3) ratio of about 4:1 to about 10:1. For example, the n−6 to n−3 fatty acid ratio can be about 6:1 to about 9:1.

The nutritional composition may also include vitamins and minerals. If the nutritional composition is intended to be a sole source of nutrition, it preferably includes a complete vitamin and mineral profile. Examples of vitamins include vitamins A, B-complex (such as B1, B2, B6 and B12), C, D, E and K, niacin and acid vitamins such as pantothenic acid, folic acid and biotin. Examples of minerals include calcium, iron, zinc, magnesium, iodine, copper, phosphorus, manganese, potassium, chromium, molybdenum, selenium, nickel, tin, silicon, vanadium and boron.

The nutritional composition can also include a carotenoid such as lutein, lycopene, zeaxanthin, and beta-carotene. The total amount of carotenoid included can vary from about 0.001 μg/ml to about 10 μg/ml. Lutein can be included in an amount of from about 0.001 μg/ml to about 10 μg/ml, preferably from about 0.044 μg/ml to about 5 μg/ml of lutein. Lycopene can be included in an amount from about 0.001 μg/ml to about 10 μg/ml, preferably about 0.0185 μg/ml to about 5 μg/ml of lycopene. Beta-carotene can comprise from about 0.001 μg/ml to about 10 mg/ml, for example about 0.034 μg/ml to about 5 μg/ml of beta-carotene.

The nutritional composition preferably also contains reduced concentrations of sodium; for example, from about 300 mg/l to about 400 mg/l. The remaining electrolytes can be present in concentrations set to meet needs without providing an undue renal solute burden on kidney function. For example, potassium is preferably present in a range of about 1180 to about 1300 mg/l; and chloride is preferably present in a range of about 680 to about 800 mg/l.

The nutritional composition can also contain various other conventional ingredients such as preservatives, emulsifying agents, thickening agents, buffers, fibres and prebiotics (e.g. fructooligosaccharides, galactooligosaccharides), probiotics (e.g. *B. animalis* subsp. lactis BB-12, *B. lactis* HN019, *B. lactis* Bi07, *B. infantis* ATCC 15697, *L. rhamnosus* GG, *L. rhamnosus* HNOOI, *L. acidophilus* LA-5, *L. acidophilus* NCFM, *L. fermentum* CECT5716, *B. longum* BB536, *B. longum* AH1205, *B. longum* AH1206, *B. breve* M16V, *L. reuteri* ATCC 55730, *L. reuteri* ATCC PTA-6485, *L. reuteri* DSM 17938), antioxidant/anti-inflammatory compounds including tocopherols, carotenoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilisers, lubricants, and so forth.

The nutritional composition can be formulated as a soluble powder, a liquid concentrate, or a ready-to-use formulation. The composition can be fed to a human in need via a nasogastric tube or orally. Various flavours, fibres and other additives can also be present.

The nutritional compositions can be prepared by any commonly used manufacturing techniques for preparing nutritional compositions in solid or liquid form. For example, the composition can be prepared by combining various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is then prepared by adding minerals, trace and ultra-trace minerals, thickening or suspending agents to water while heating and stirring. The resulting solution is held for 10 minutes with continued heat and agitation before adding carbohydrates (e.g. the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packed to form an aseptically packaged nutritional composition. In this form, the nutritional composition can be in ready-to-feed or concentrated liquid form. Alternatively, the composition can be spray-dried and processed and packaged as a reconstitutable powder.

When the nutritional product is a ready-to-feed nutritional liquid, it may be preferred that the total concentration of HMOs in the liquid, by weight of the liquid, is from about 0.1% to about 1.5%, including from about 0.2% to about 1.0%, for example from about 0.3% to about 0.7%. When the nutritional product is a concentrated nutritional liquid, it may be preferred that the total concentration of HMOs in the liquid, by weight of the liquid, is from about 0.2% to about 3.0%, including from about 0.4% to about 2.0%, for example from about 0.6% to about 1.5%.

In another embodiment, the nutritional composition is in a unit dosage form. The unit dosage form can contain an acceptable food-grade carrier, e.g. phosphate buffered saline solution, mixtures of ethanol in water, water and emulsions such as an oil/water or water/oil emulsion, as well as various wetting agents or excipients. The unit dosage form can also contain other materials that do not produce an adverse, allergic or otherwise unwanted reaction when administered to a human. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents.

A unit dosage form of this invention can be administered orally, e.g. as a tablet, capsule, or pellet containing a predetermined amount of the mixture, or as a powder or granules containing a predetermined concentration of the mixture or a gel, paste, solution, suspension, emulsion, syrup, bolus, electuary, or slurry, in an aqueous or non-aqueous liquid, containing a predetermined concentration of the mixture. An orally administered composition can include one or more binders, lubricants, inert diluents, flavouring agents, and humectants. An orally administered composition such as a tablet can optionally be coated and can be formulated to provide sustained, delayed or controlled release of the HMO.

A unit dosage form of this invention can also be administered by naso-gastric tube or direct infusion into the GI tract or stomach.

A unit dosage form of this invention can also include therapeutic agents such as antibiotics, probiotics, analgesics, and anti-inflammatory agents. The proper dosage of such a composition for a human can be determined in a conventional manner, based upon factors such as the human's condition, immune status, body weight and age. In some cases, the dosage will be at a concentration similar to that found for the HMOs of the composition in human breast milk. The required amount would generally be in the range from about 1 g to about 15 g per day, in certain embodiments from about 2 g to about 10 g per day, for example about 3 g to about 7 g per day. Appropriate dose regimes can be determined by methods known to those skilled in the art.

In further embodiment, the HMO can be formulated as a pharmaceutical composition. The pharmaceutical composition can contain a pharmaceutically acceptable carrier, e.g. phosphate buffered saline solution, mixtures of ethanol in water, water and emulsions such as an oil/water or water/oil emulsion, as well as various wetting agents or excipients. The pharmaceutical composition can also contain other materials that do not produce an adverse, allergic or otherwise unwanted reaction when administered to non-infants. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents.

The pharmaceutical compositions can be administered orally, e.g. as a tablet, capsule, or pellet containing a predetermined amount, or as a powder or granules containing a predetermined concentration or a gel, paste, solution, suspension, emulsion, syrup, bolus, electuary, or slurry, in an aqueous or non-aqueous liquid, containing a predetermined concentration. Orally administered compositions can include binders, lubricants, inert diluents, flavouring agents, and humectants. Orally administered compositions such as tablets can optionally be coated and can be formulated to provide sustained, delayed or controlled release of the mixture therein.

The pharmaceutical compositions can also be administered by rectal suppository, aerosol tube, naso-gastric tube or direct infusion into the GI tract or stomach.

The pharmaceutical compositions can also include therapeutic agents such as antibiotics, probiotics, analgesics, and anti-inflammatory agents. The proper dosage of these compositions for a human can be determined in a conventional manner, based upon factors such condition, immune status, body weight and age. In some cases, the dosage will be at a concentration similar to that found for the HMOs in human breast milk. The required amount would generally be in the range from about 1 g to about 15 g per day, in certain embodiments from about 2 g to about 10 g per day, for example from about 3 g to about 7 g per day. Appropriate dose regimes can be determined by conventional methods.

For the treatment of non-coeliac wheat and/or gluten sensitivity in human, the amount of HMO(s) required to be administered will vary depending upon factors such as the risk and severity of the fatigue, any underlying medical condition or disease, age, the form of the composition, and other medications being administered. Further the amount may vary depending upon whether the HMOs are being used to reduce active symptoms (when the dose may be higher) or whether the HMOs are being used to induce tolerance and/or as a secondary prevention (when the dose may be lower). However, the required amount can be readily set by a medical practitioner and would generally be in the range from about 1 g to about 15 g per day, in certain embodiments from about 2 g to about 10 g per day, for example from about 3 g to about 7 g per day. An appropriate dose can be determined based on several factors, including, for example, body weight and/or condition, the severity of the non-coeliac wheat and/or gluten sensitivity being treated or prevented, other ailments and/or diseases, the incidence and/or severity of side effects and the manner of administration. Appropriate dose ranges may be determined by methods known to those skilled in the art. For example, for treating non-coeliac wheat and/or gluten sensitivity in a human, the dosing can be around 3 g to around 15 g per day, preferably 4 g to 10 g per day, whereas for inducing wheat and/or gluten tolerance or in secondary prevention, the dosing can be around 2 g to around 7.5 g per day, preferably 2 g to 5 g per day. In a combined treatment protocol, during an initial treatment phase for treating non-coeliac wheat and/or gluten sensitivity (first phase), the dosing can be higher (for example 3 g to 15 g per day, preferably 4 g to 7.5 g per day), which is followed by a phase for inducing wheat and/or gluten tolerance or secondary prevention (second phase), the dosing can be reduced (for example, 2 g to 7.5 g per day, preferably 2 g to 5 g per day).

EXAMPLES

Example 1

A total of 40 male and female patients are recruited to participate in the study. Each patient is self-diagnosed with wheat and/or gluten sensitivity. The participants complete a baseline screening survey where they indicate any other medical conditions, and the severity of various gastrointestinal and quality of life symptoms. For measuring the symptoms, a 5-point Likert scale is used where a score of 1 means "no symptoms" and a score of 5 means "severe symptoms".

Each participant is provided with an amount of HMO sufficient for 3 weeks of a daily dose of about 4 g of HMO. The HMO is provided as either 2'-FL alone or a 4:1 mix of 2'-FL and LNnT (by weight). The participants maintain their normal diet.

After 3 weeks of intake, each participant completes a second survey where they indicate the severity of various gastrointestinal and quality of life symptoms. The same 5-point Likert scale is used to assess the symptoms.

Each participant is then provided with an additional amount of HMO sufficient for another 3 weeks of a daily dose of about 4 g of HMO. The process is repeated after 6 weeks, 9 weeks and 12 weeks.

Over the course of the 12 weeks, the participants indicate a reduction in gastrointestinal symptoms; especially pain, diarrhoea, bloating and gas. Furthermore, the patients indicate an improvement in fatigue.

Example 2

Non-coeliac wheat sensitivity patients of age between 18-75 years are recruited from gastroenterological outpatient centre using the non-coeliac gluten sensitivity consensus criteria. Patients are excluded if they are positive for the coeliac disease-specific IgA anti-endomysial and/or anti-TG2 antibody or if they present histological findings characteristic of coeliac disease. Further, patients are excluded if they are positive for wheat allergy specific IgE serology or skin prick test. Other exclusion criteria are inflammatory bowel diseases, psychiatric disorders, major abdominal surgery (in particular intestinal resections), diabetes mellitus, systemic autoimmune diseases, previous anaphylactic episodes, any systemic disorders, pregnant or breast-feeding women, and patients already on pharmacological therapy.

At an initial visit (screening), each patient is given both written and oral information about the study and the patient is asked to sign an informed consent form. Each patient is evaluated by a full review of clinical history, and a blood sample for eligibility analysis is collected. Equipment for faecal sampling is distributed to each patient. Patients are instructed to keep their samples in the freezer until the next visit. Each patient is educated on a gluten-free diet. The diet is illustrated by dedicated medical personnel and each patient is provided with flyers describing the diet, listing allowed and not allowed foods and advising on the way to read the food labels. The patients are also given direct contact links (by e-mail and telephone) to their enrolment centres for any query about their diet.

A total of 80 patients are included. The patients are randomised into two groups, each of 40 patients, with one group consuming the treatment product and one group the placebo product for 8 weeks. The treatment product contains 5 grams of a combination of 2'-FL and LNnT while the placebo product contains 5 grams of glucose. Both products are in powder form in a unit dosage container.

At a second visit (beginning of intervention), eligibility criteria are checked, and eligible subjects are randomised to the two arms in the trial. An assessment is made of symptoms of physical and mental health, gastrointestinal symptoms, quality of life, and faecal consistency (as measured by SF36, GSRS, BSFS and QoL questionnaires). Trial supplementation is distributed along with instructions on use of an electronic compliance diary. The faecal samples are collected and equipment for collecting new samples is distributed. Patients are placed on a strict gluten-free diet for 8 weeks.

Blood samples are collected for biomarker and immune cell studies and biobanking. The serum from the blood samples is transferred to cryotubes and stored at −80° C. The following biomarkers are measured: TNF-α, IL-1β, IL-8, IL-6, IL-12, IL-10, MIP-1β, hs-CRP, lipopolysaccharide binding protein, fatty acid binding protein 2, tryptase, anti-flagellin, zonulin, histamine, prostaglandin 2 and cortisol. Flow cytometry are performed on blood to determine the level of immune cells.

The faecal samples are stored at −80° C. until analysis. Microbiological analysis is performed on the faecal samples using the 16S rRNA gene sequence.

At a third visit after 8 weeks, the faecal samples are collected, blood samples are collected, and an assessment is made of symptoms of physical and mental health, gastrointestinal symptoms, quality of life, and faecal consistency (as measured by SF36, GSRS, BSFS and QoL questionnaires). Trial supplementation and equipment for collecting new samples is distributed. Each patient is then placed on a gluten-containing diet corresponding to a daily dose of 10 g of gluten for a period of 1 week.

At the end of the intervention (week 9), each patient has a visit with the medical team. A physical examination is done and symptoms (as measured by GSRS, IBS-SSS, BSFS and QoL scales etc.) are reassessed. Trial supplementation products are collected to check compliance. Faecal samples and blood samples are collected and analysed as before.

The patients receiving the treatment product report a reduction in GSRS score and an improvement in faecal consistency as compared to the placebo group. Analysis of the blood indicates that the treatment patients have reduced levels of inflammatory markers, reduced gut permeability indicating an improved mucosal barrier, and an increase in regulatory immune cells. The faecal analysis indicates that the treatment patients have reduced levels of bacterial overgrowth/dysbiosis and a higher level of bifidobacteria, especially members of the *Bifidobacterium adolescentis* phylogenetic group, *Bifidobacterium longum* and *Bifidobacterium bifidum*.

Example 3

2'-FL and LNnT are tested with respect to their ability to induce MUC2, TFF3, EIMβ, CHST5, and GAL3ST2 expression in the human LS174T cell culture model of goblet cells. The human LS174T cell line is obtained from the American Type Culture Collection (ATCC). LS174T cells are maintained in minimum essential medium (MEM) supplemented according to instructions at 37° C. in air containing 5% of $CO_2$. 2'-FL and LNnT are dissolved in cell culture grade water to the required concentration. The LS174T cells are treated with the HMO solution containing 0 or 5 mg HMO/ml.

The LS174T cells are collected and suspended in Trizol reagent and total RNA is isolated using an RNA analysis kit (Qiagen) according to the manufacturer's instructions and the RNA isolates are quantified using Nanodrop analysis (Thermo Fisher Scientific). RNA isolates are reverse transcribed using a high capacity cDNA Reverse Transcription Kit (Applied Biosystems) to create cDNA, which is then used to assess gene expression via quantitative RT-PCR.

For the quantitative RT-PCR, specific TaqMAN gene expression assays are obtained from Applied Biosystems, which include expression assays for MUC2, TFF3, CHST5 and GAL3ST2. Quantitative real-time PCR is performed using TaqMAN PCR Master Mix (Applied Biosystems). Reactions are run in duplicates in a 384-well plate using an Applied Biosystems 7900HT Fast Real-Time PCR System. The results are analysed using SDS 2.3 software and calculated by delta Ct method. All samples are normalized to Gus-β expression and fold induction is calculated over untreated controls. Gene expression is expressed as fold increase compared to HMO-free control cells. The experiment is repeated three times.

The results indicate that treatment with 2'-FL and LNnT increases the expression of the MUC2 and TFF3 genes compared to control cultures. Increased expression of goblet cell genes is specific and not universal, as evidenced by the minimal induction or lack of induction of CHST5 and GAL3ST2, respectively. MUC2 and TFF3 are key components of the mucosal barrier and improve mucosal barrier function.

Example 4

The HMOs 2'-FL and LNnT are introduced into a rotary blender in a 4:1 mass ratio. An amount of 0.25 w % of magnesium stearate is introduced into the blender and the mixture blended for 10 minutes. The mixture is then agglomerated in a fluidised bed and filled into 5 gram stick packs and the packs are sealed.

The invention claimed is:

1. A method of inducing wheat and/or gluten tolerance in a human patient suffering from non-coeliac wheat and/or gluten sensitivity comprising administering at least one human milk oligosaccharides (HMO) to the patient,
wherein the at least one HMO comprises 2'-FL, DFL, LNT, or LNnT.

2. The method according to claim 1, wherein the at least one HMO is administered in a synthetic composition.

3. The method according to claim 2, wherein the synthetic composition comprises an amount of 1 g to 15 g of the at least one HMO.

4. The method according to claim 1, wherein the at least one HMO further comprises 3'-SL, 6'-SL, LNFP-I, or a mixture thereof.

5. The method according to claim 1, wherein the at least one HMO is a mixture of a fucosylated HMO and a non-fucosylated HMO.

6. The method according to claim 5, wherein the mixture comprises at least one of 2'-FL and DFL, and at least one of LNnT and LNT.

7. The method according to claim 6, wherein the mixture comprises 2'-FL and LNnT.

8. The method according to claim 1, wherein the patient is administered an amount of 3 g to 15 g per day of the at least one HMO.

9. The method according to claim 1, wherein at least one HMO is administered to the human for at least 7 consecutive days.

10. The method according to claim 1, in which the patient is administered the at least one HMO while consuming gluten containing cereals.

11. The method according to claim 1, the method comprises administering the at least one HMO at a first dose in a first phase to treat non-coeliac wheat and/or gluten sensitivity and administering the at least one HMO at a second dose in a second phase for inducing the wheat and/or gluten tolerance.

12. The method according to claim 11, in which the patient is administered a higher dose of HMO during the first phase followed by a lower dose of HMO during the second phase.

13. The method according to claim 12, in which the higher dose is about 3 g to about 15 g per day and the lower dose is about 2 g to about 7.5 g per day.

14. The method according to claim 11, wherein the duration of the first phase is at least consecutive 7 days, and the duration of the second phase is at least four consecutive weeks.

15. The method according to claim 3, wherein the synthetic composition comprises an amount of 2 g to 10 g of the at least one HMO.

16. The method according to claim 3, wherein the synthetic composition comprises an amount of 3 g to 7 g of the at least one HMO.

17. The method according to claim 7, wherein the 2'-FL and LNnT in the mixture are in a mass ratio of 4:1 to 1:1.

18. The method according to claim 8, wherein the patient is administered about 4 g to about 7.5 g of the at least one HMO per day.

19. The method according to claim 13, in which the higher dose is about 4 g to about 7.5 g per day and the lower dose is about 2 g to about 5 g per day.

* * * * *